(12) United States Patent
Binier (10) Patent No.: US 9,789,260 B1
(45) Date of Patent: Oct. 17, 2017

(54) DEVICE AND SYSTEM FOR DRUG INFORMATION DETECTION

(71) Applicant: INNOVATIVE PRECISION INSTRUMENTS LIMITED, Hong Kong (HK)

(72) Inventor: Richard Jean Marie Binier, Hong Kong (HK)

(73) Assignee: INNOVATIVE PRECISION INSTRUMENTS LIMITED, Hong Kong (HK)

( * ) Notice: Subject to any disclaimer, the term of this patent is extended or adjusted under 35 U.S.C. 154(b) by 0 days.

(21) Appl. No.: 15/605,822

(22) Filed: May 25, 2017

(51) Int. Cl.
*A61M 5/31* (2006.01)
*A61M 5/315* (2006.01)

(52) U.S. Cl.
CPC ...... *A61M 5/31568* (2013.01); *A61M 5/3157* (2013.01); *A61M 5/31533* (2013.01); *A61M 5/31546* (2013.01); *A61M 5/31573* (2013.01); *A61M 5/31593* (2013.01); *A61M 2205/3584* (2013.01); *A61M 2205/502* (2013.01); *A61M 2205/52* (2013.01); *A61M 2205/582* (2013.01); *A61M 2205/587* (2013.01); *A61M 2205/8206* (2013.01)

(58) Field of Classification Search
CPC ............ A61M 5/31568; A61M 5/3157; A61M 5/31533; A61M 2205/582
See application file for complete search history.

(56) References Cited

U.S. PATENT DOCUMENTS

| | | | |
|---|---|---|---|
| 3,886,934 A * | 6/1975 | Doty | A61H 23/02 601/18 |
| 9,101,723 B2 | 8/2015 | Larsen | |
| 2010/0286612 A1 | 11/2010 | Cirillo et al. | |
| 2012/0053527 A1 | 3/2012 | Cirillo et al. | |
| 2012/0065588 A1 | 3/2012 | Cirillo et al. | |
| 2014/0005950 A1 | 1/2014 | Groeschke et al. | |
| 2015/0202376 A1 | 7/2015 | Haupt | |
| 2015/0202377 A1 | 7/2015 | Haupt | |
| 2016/0129182 A1 | 5/2016 | Schuster et al. | |
| 2016/0213853 A1* | 7/2016 | Despa | A61M 5/31548 |
| 2017/0182258 A1* | 6/2017 | Michael | A61M 5/31568 |

* cited by examiner

*Primary Examiner* — Nathan R Price
*Assistant Examiner* — Courtney Frederickson
(74) *Attorney, Agent, or Firm* — Kramer Amado, P.C.

(57) ABSTRACT

An injected dose detection device which includes a housing having a joint surface surrounding an injection device and a through hole formed on the joint surface configured to communicate with an internal part of the housing, a vibration sensor disposed in the internal part of the housing configured to detect at least one vibration signal based on a minimum vibration threshold, a vibration transmitting element positioned directly between the vibration sensor and the injection device and configured to transmit the at least one vibration signal and a processing unit configured to process the at least one vibration signal for generating injected dose information corresponding to the injected dose.

20 Claims, 5 Drawing Sheets

DEVICE AND SYSTEM FOR DRUG INFORMATION DETECTION

TECHNICAL FIELD

This disclosure relates generally to a drug delivery device for injection of a drug and more particularly, but not exclusively, a drug information detection device for detecting drug dosage information.

BACKGROUND OF THE INVENTION

Self-injections of medications have become increasingly common and various types of injection pens have been developed as a result.

While many types have been developed, generally, an injection pen comprises an injected dose adjusting knob and an injection unit. The injected dose adjusting knob is configured to adjust and set an injected dose of medication for the user.

The injection unit is configured to perform an injection according to the injected dose set by the injected dose adjusting knob by the user. For example, a common type of injection pen is an injection pen with a plunger, where the injection unit comprises a plunger which is configured to expel medication out of a needle for injection.

The user can set the amount of medication to be injected by rotating the adjusting knob to a predetermined graduation mark which corresponds to a change in the moving distance of the plunger. When a user presses the injected dose adjusting knob, the internal mechanisms of the injection devices press the plunger to a predetermined position for completing the injection of the set of amount of medication. These internal mechanisms vary among a number of alternative injection devices.

For disease management of a patient, it is critical that not only is a correct dose administered but that the correct dose is administered at a correct date and time.

For example, in a diabetic user, it is critical to inject insulin at a correct dose at a correct time.

In order to ensure the necessary effect of insulin, medical staff will encourage a patient with diabetes to record an injected dose and injection time for each injection.

However, the prior art injection device cannot record the injected dose and the injection time of the medication. The user is responsible for recording the injected dose of medication and the injection time in a notebook by handwriting or other record. If the user forgets to record the injection information or records the injection information incorrectly, the medical staff will have incorrect information for further diagnosis and treatment.

Some detection devices use a sensor to detect the moving distance of the plunger, and convert a detection result into electronic data.

In that approach, a computation result is directly affected by detection of the moving distance of the plunger and therefore the detection device requires high accuracy and requires complex operations, such that detection errors may occur. Additionally, a detection device for detecting the moving distance of the plunger must be integral to the injection device and thus increases the cost and complexity of the injection device.

There is a need for a detecting device and system that may be used with multiple different injection devices while accurately detecting the injected dose of the injection device.

SUMMARY OF THE INVENTION

A brief summary of various embodiments is presented below. Embodiments address the need to create a drug information detection device configured to record dose information by detecting the number of vibrations emitted by the injection pen.

In order to overcome these and other shortcomings of the prior art and in light of the present need to create drug information detection device configured to record dose information by detecting the number of vibrations emitted by the injection pen, a brief summary of various exemplary embodiments is presented. Some simplifications and omissions may be made in the following summary, which is intended to highlight and introduce some aspects of the various exemplary embodiments, but not to limit the scope of the invention.

Detailed descriptions of a preferred exemplary embodiment adequate to allow those of ordinary skill in the art to make and use the inventive concepts will follow in later sections.

Various embodiments relate to an injected dose detection device including a housing having a joint surface surrounding an injection device and a through hole formed on the joint surface configured to communicate with an internal part of the housing, a vibration sensor disposed in the internal part of the housing configured to detect at least one vibration signal based on a minimum vibration threshold, a vibration transmitting element positioned directly between the vibration sensor and the injection device and configured to transmit the at least one vibration signal and a processing unit configured to process the at least one vibration signal for generating injected dose information corresponding to the injected dose.

In an embodiment of the present disclosure, the injected dose detection device further includes a storage device electrically connected to the processing unit configured to store the injected dose information.

In an embodiment of the present disclosure, the injected dose detection device further includes a wireless communication module electrically connected to the processing unit configured to wirelessly transmit the injected dose information to an electronic device.

In an embodiment of the present disclosure, the injected dose detection device further includes a display electrically connected to the processing unit configured to display the injected dose information.

In an embodiment of the present disclosure, the injected dose detection device further includes at least one adjusting button electrically connected to the processing unit configured to adjust the injected dose information.

In an embodiment of the present disclosure, the injected dose detection device further includes a power switch electrically connected to the processing unit, a battery electrically connected to the power switch and a light emitting diode electrically connected to the processing unit for indicating an operation status.

In an embodiment of the present disclosure, a bottom plate and a side wall of the vibration transmitting element form a shell structure to cover the vibration sensor and the vibration sensor contacts the inner surface of the bottom plate, and the injection device contacts the outer surface of the bottom plate.

In an embodiment of the present disclosure, the electronic device is a server, a smart phone, a laptop computer, or a personal computer.

In an embodiment of the present disclosure, the processing unit is configured to change the minimum vibration threshold based on the frequency at which the at least one adjusting button is pressed, and the minimum vibration threshold is a minimum amplitude of the vibrational signal.

In an embodiment of the present disclosure the minimum vibration threshold is decreased when the adjusting button is pushed to increase the number of injected doses and the minimum vibration threshold is increased when the adjusting button is pushed to decrease the number of injected doses.

Various embodiments relate to an injected dose detection system, including an injection device; and an injected dose detection device, including a housing having a joint surface surrounding the injection device and a through hole formed on the joint surface configured to communicate with an internal part of the housing, a vibration sensor disposed in the internal part of the housing configured to detect at least one vibration signal based on a minimum vibration threshold, a vibration transmitting element positioned directly between the vibration sensor and the injection device and configured to transmit the at least one vibration signal and a processing unit configured to process the at least one vibration signal for generating injected dose information corresponding to the injected dose.

In an embodiment of the present disclosure, the injected dose detection system further includes a storage device electrically connected to the processing unit configured to store the injected dose information.

In an embodiment of the present disclosure, the injected dose detection system further includes a wireless communication module electrically connected to the processing unit configured to wirelessly transmit the injected dose information to an electronic device.

In an embodiment of the present disclosure, the injected dose detection system, further includes a display electrically connected to the processing unit configured to display the injected dose information.

In an embodiment of the present disclosure, the injected dose detection system, further includes at least one adjusting button electrically connected to the processing unit configured to adjust the injected dose information.

In an embodiment of the present disclosure, the injected dose detection system, further includes a power switch electrically connected to the processing unit, a battery electrically connected to the power switch, and a light emitting diode electrically connected to the processing unit for indicating an operation status.

In an embodiment of the present disclosure, a bottom plate and a side wall of the vibration transmitting element form a shell structure to cover the vibration sensor, and the vibration sensor contacts the inner surface of the bottom plate, and the injection device contacts the outer surface of the bottom plate.

In an embodiment of the present disclosure, the electronic device is a server, a smart phone, a laptop computer, or a personal computer.

In an embodiment of the present disclosure, the processing unit is configured to change the minimum vibration threshold based on the frequency at which the at least one adjusting button is pressed and the minimum vibration threshold is a minimum amplitude of the vibrational signal.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

These and other more detailed and specific features of the present invention are more fully disclosed in the following specification, reference being had to the accompanying drawings, in which.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. Descriptors such as "first," "second," "third," etc., are not meant to limit the order of elements discussed, are used to distinguish one element from the next, and are generally interchangeable.

An object of the present invention is to provide an injected dose detection device 10 and an injected dose detection system 20, in order to solve detection error problems of the prior art.

The present invention provides an injected dose detection device 10 which may be detachably attached to an injection device 200 for detecting an injected dose of the injection device 200.

The injection device 200 may generate at least one vibration signal while a user sets the injected dose. Alternative injection devices may also include internal tactile and/or auditory signaling mechanisms to indicate dose adjustments to a user, which create vibrations in the injection device 200.

The injected dose detection device 10 may include a housing 100 which may include a joint surface 108 which may surround the injection device 200 and a through hole 110 formed on the joint surface 108 which may communicate with an internal part of the housing.

The vibration sensor 102 may be arranged in the internal part of the housing 100 and may detect at least one vibration signal.

The vibration transmitting element 104 may be positioned to pass through the through hole 110 which allows the two ends of the vibration transmitting element 104 to respectively abut against the vibration sensor 102 and the injection device 200. The vibration transmitting element 104 may be configured to transmit the at least one vibration signal to the vibration sensor 102 and the processing unit 106.

The processing unit 106 may be configured to process the at least one vibration signal for generating injected dose information corresponding to the injected dose.

Figure 1:
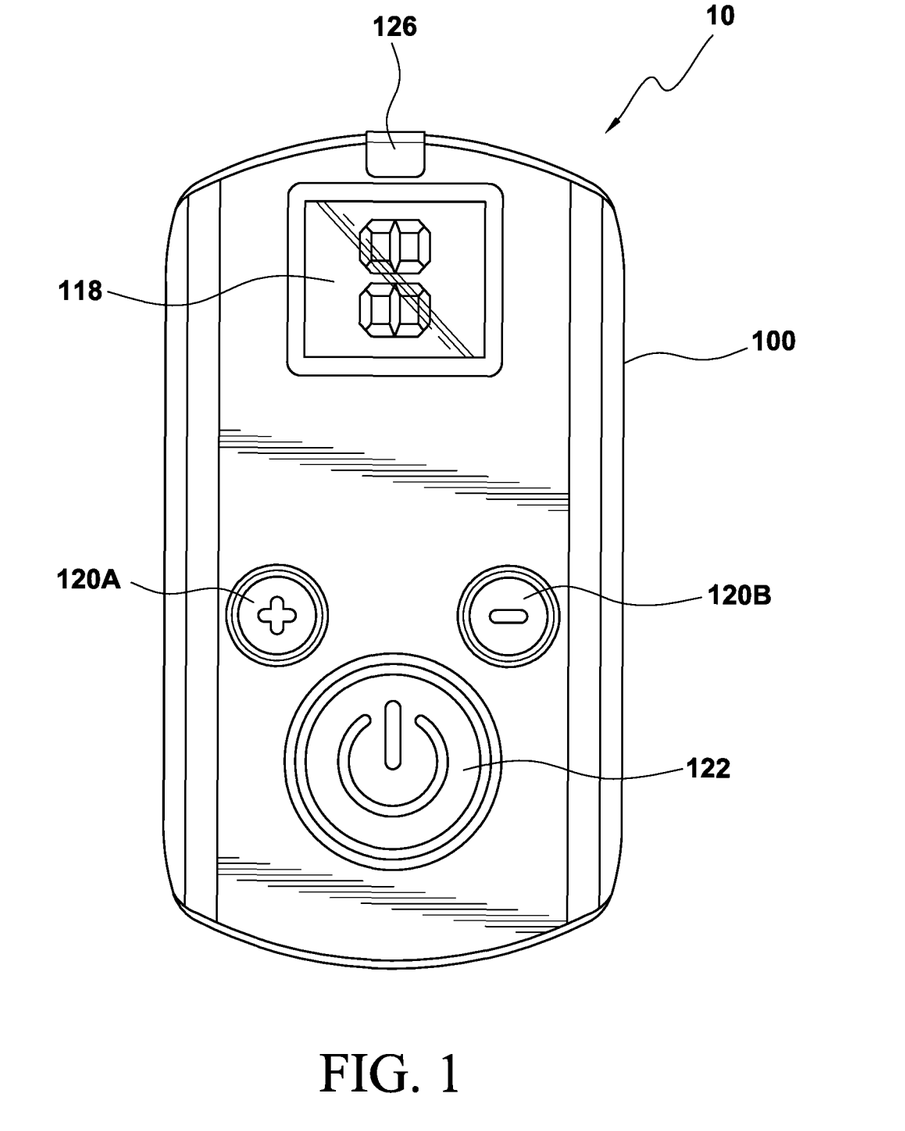
FIG. 1 illustrates an injected dose detection device according to an embodiment of the present invention.

FIG. 1 is a diagram showing an injected dose detection device 10 according to an embodiment of the present invention. The injected dose detection device 10 may be detachably attached to an injection device 200 for detecting an injected dose of the injection device 200.

The injection device 200 may generate at least one vibration signal while a user sets the injected dose, by rotating an adjusting knob with gradation marks to set the amount of the dosage.

The injected dose detection device 10 may include a housing 100, a vibration sensor 102, a vibration transmitting element 104 and a processing unit 106.

Figure 2:
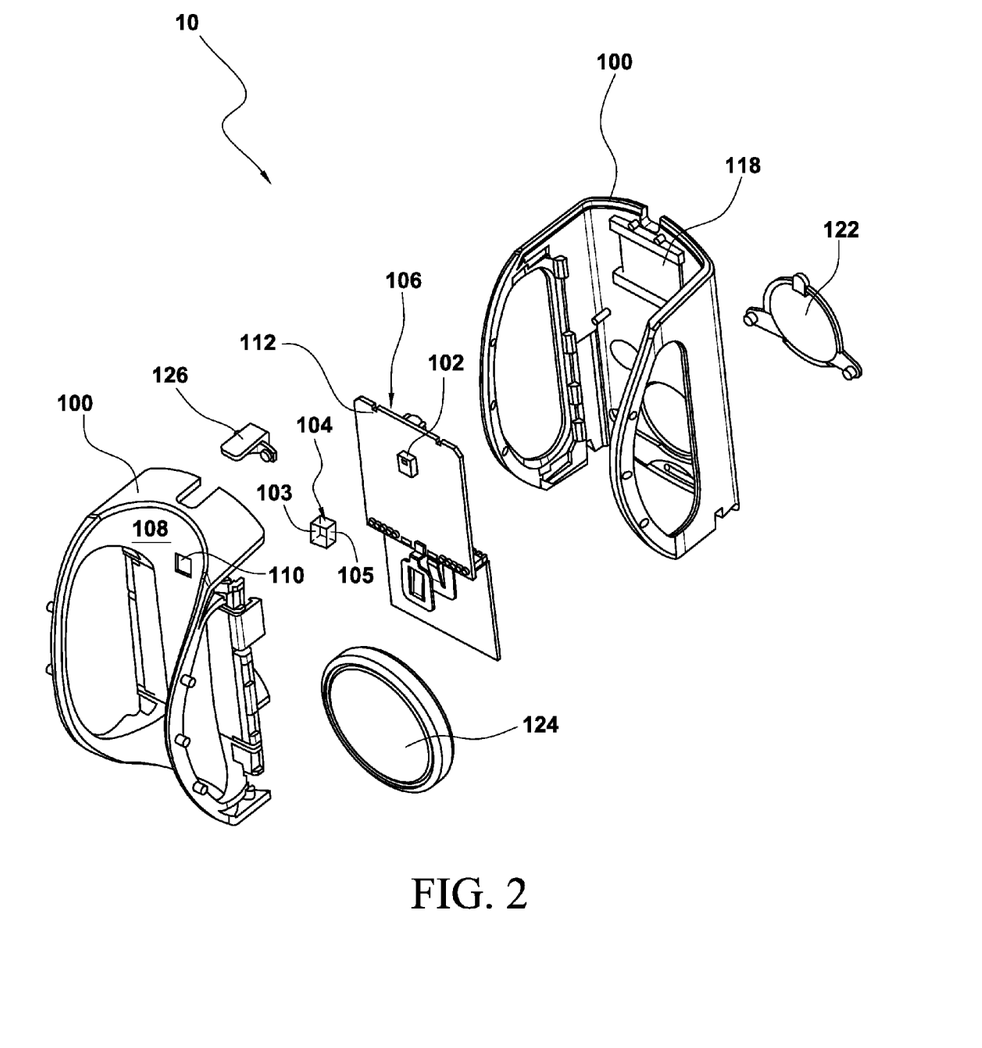
FIG. 2 illustrates an exploded view of the injected dose detection device of FIG. 1.

FIG. 2 is an exploded view of the injected dose detection device 10. The housing 100 may include a joint surface 108 which may surround and cradle the injection device 200, and a through hole 110 which may be formed on the joint surface 108 and which may communicate with an internal part of the housing 100.

The vibration sensor 102 may be arranged in the internal part of the housing 100 for detecting the at least one vibration signal. The vibration transmitting element 104 may pass through the through hole 110 which allows the two ends of the vibration transmitting element 104 to respectively abut against the vibration sensor 102 and the injection device 200.

The vibration transmitting element 104 may transmit the at least one vibration signal to the vibration sensor 102 and the processing unit 106.

The vibration transmitting element 104 may also include a bottom plate 103 and a side wall 105. The bottom plate 103 and the side wall 105 may form a shell structure to cover the surroundings of the vibration sensor 102.

The shell structure may be a cuboid and the vibration transmitting element 104 may be made of a metal, but the vibration transmitting element 104 may be any shape and the shell structure may be any shape that fits the shape of the vibration sensor 102.

The processing unit 106 may process the at least one vibration signal to generate injected dose information corresponding to the injected dose. The processing unit 106 includes a circuit board 112 and a microprocessor (not illustrated).

The vibration sensor 102 may measure vibrations from the injection device 200 and transform that vibration into digital signals by the processing unit 106 (e.g. a voltage oscillograph).

The minimum vibration threshold may be set to the minimum amplitude of the digital signal equivalent to one dosage click.

The minimum vibration threshold may be set to the minimum amplitude of 0.3 volts, as the minimum vibration threshold may vary depending on the injection device. When the amplitude of the digital signal is greater than or equal to 0.3 volts, then the processing unit 106 registers a dose adjustment of the injection device 200. When the amplitude of the digital signal is less than 0.3 volts, the processing unit 106 will not register it as a dose adjustment of the injection device 200. For example, if the injection device 200 includes a click mechanism for indicating dose adjustments to the user, the processing unit 106 would register clicks generating a vibration corresponding to a minimum amplitude of 0.3 volts as a dose adjustment.

The processing unit 106 may include a machine learning function which may autocorrect with the time and usage of the injection device 200 based on the user's manual correction history.

For example, the processing unit 106 may set its own minimum vibration threshold based on the user and the injection device 200. If a user presses the (+) adjusting button 120 in a sequence of use (for example, 10 times in a 100 uses), then the processing unit will decrease the minimum vibration threshold to 0.295 volts because the processing unit 106 excludes valid inputs. Inversely, if a user presses the (−) adjusting button 120 in a sequence of use (for example, 10 times in a 100 uses), then the processing unit will increase the minimum vibration threshold to 0.305 volts because the processing unit 106 includes invalid inputs.

Figure 3:
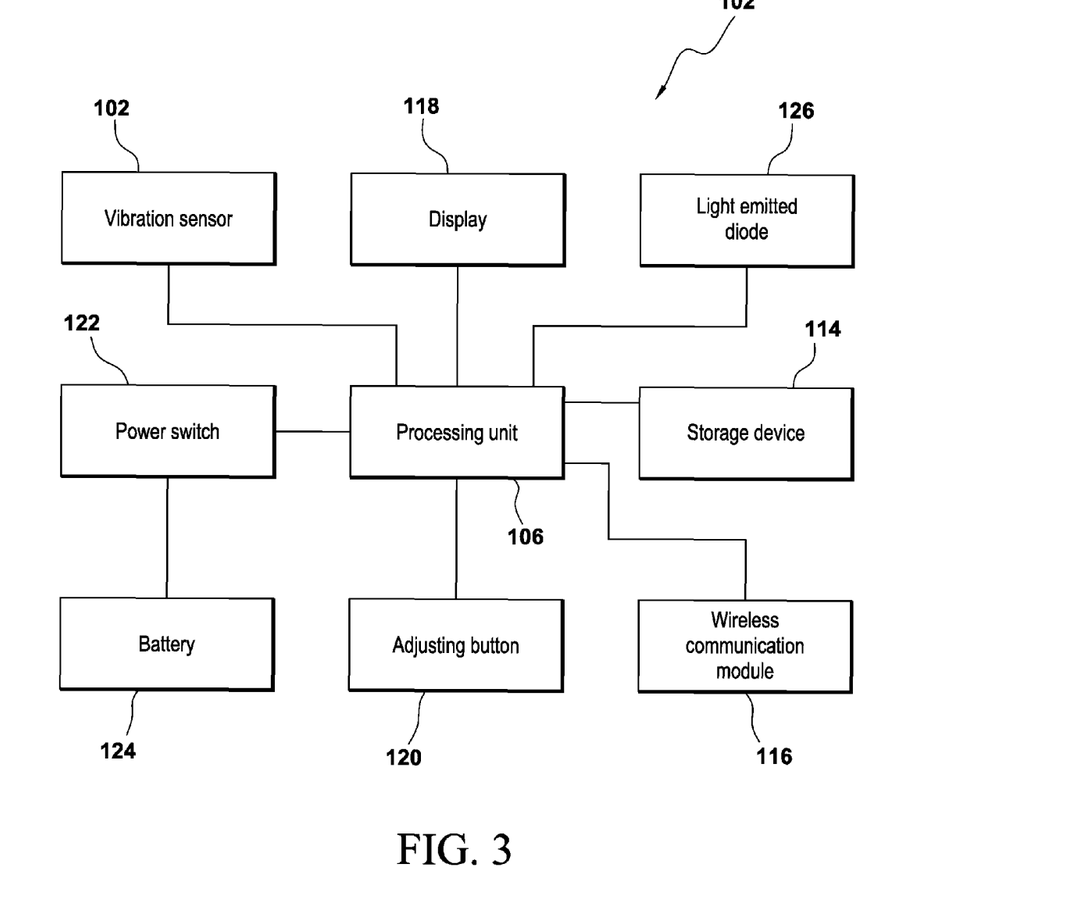
FIG. 3 illustrates a block diagram of the injected dose detection device of FIG. 1.

FIG. 3 is a block diagram of the injected dose detection device 10. The injected dose detection device 10 includes a storage device 114, a wireless communication module 116, a display 118, at least one adjusting button 120, a power switch 122, a battery 124 and a light emitting diode 126.

The storage device 114 is electrically connected to the processing unit 106 and may store the injected dose information generated by the processing unit 106.

The wireless communication module 116 is electrically connected to the processing unit 106 and may wirelessly transmit the injected dose information to an electronic device (not illustrated).

The electronic device may be a server, a smart phone, a laptop computer, a personal computer or any other electronic device.

The display 118 is electrically connected to the processing unit 106 and may display the injected dose information.

The adjusting button 120 is electrically connected to the processing unit 106 and may adjust the injected dose information. The adjusting button 120 may include an upper adjusting button 120A and a lower adjusting button 120B for allowing a user to manually adjust the injected dose information when the injected dose detected by the injected dose detection device 10 is greater than or less than the injected dose set by the user.

The power switch 122 is electrically connected to the processing unit 106.

The battery 124 is electrically connected to the power switch 122.

The light emitting diode 126 is electrically connected to the processing unit 106 and may indicate an operation status (i.e. indicating whether the injected dose information has been stored, low battery power, etc.).

Figure 4:
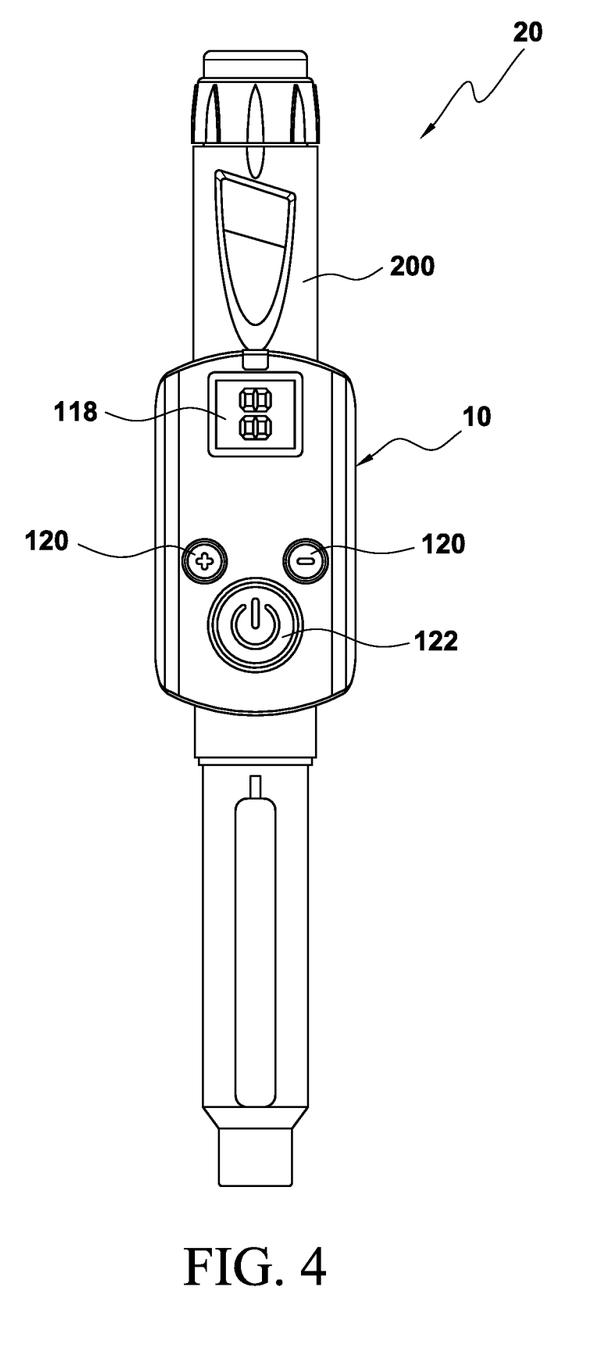
FIG. 4 illustrates a diagram showing an injected dose detection system comprising the injected dose detection device of FIG. 1.

FIG. 4 is a diagram showing an injected dose detection system comprising the injected dose detection device 10. The injected dose detection system 20 includes an injection device 200 and the injected dose detection device 10. The injected dose detection device 10 may be detachably attached to the injection device 200 for detecting an injected dose of the injection device 200. The injection device 200 may generate at least one vibration signal while the user sets the injected dose.

Figure 5:
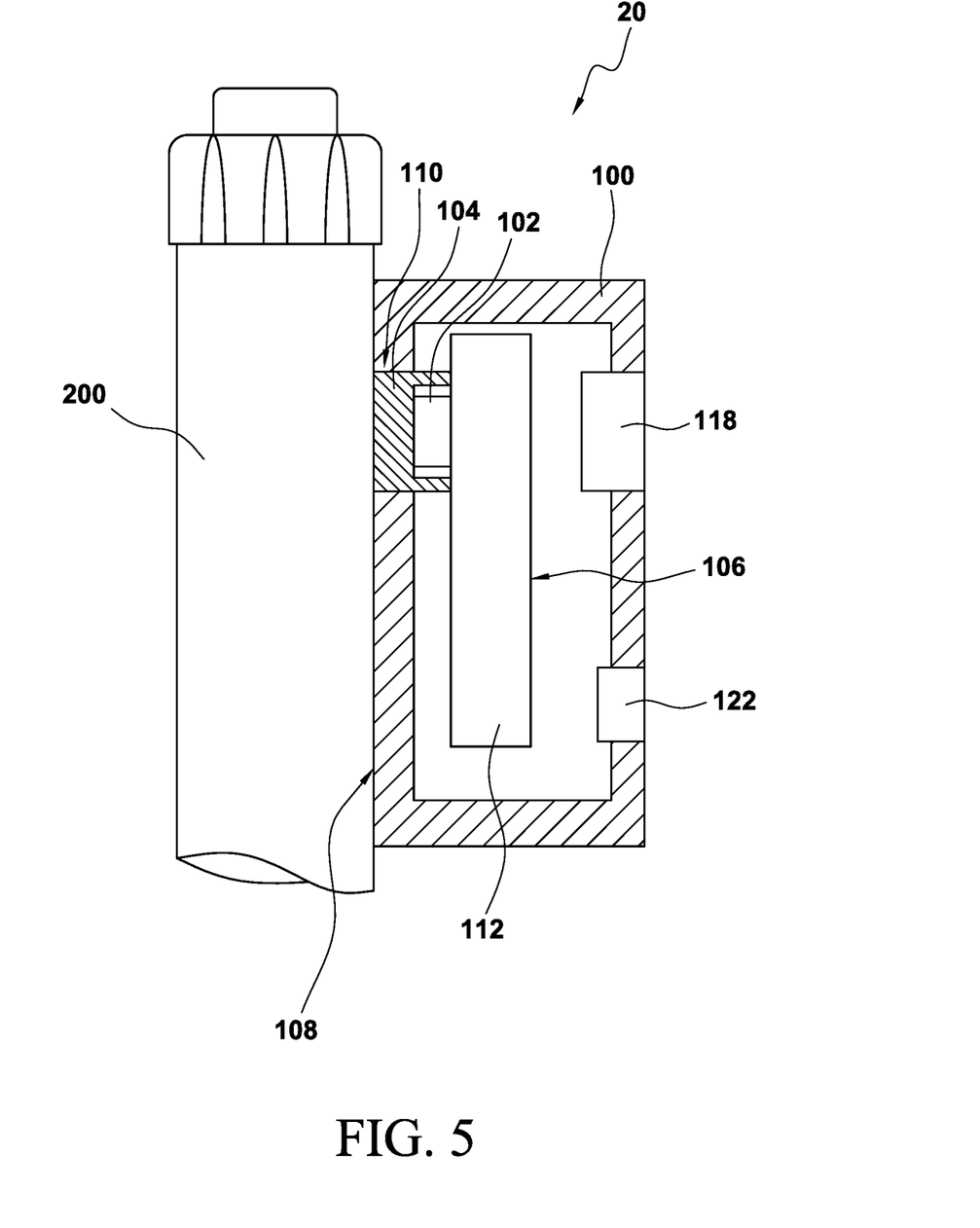
FIG. 5 illustrates a partial cross-sectional view of the injected dose detection system.

FIG. 5 is a partial cross-sectional view of the injected dose detection system 20. The housing 100 has the joint surface 108 which may surround the injection device 200, and the through hole 110 formed on the joint surface 108 and communicating with the internal part of the housing 100.

The vibration sensor 102 may be arranged in the internal part of the housing 100 for detecting the at least one vibration signal.

The vibration transmitting element 104 may pass through the through hole 110 for allowing two ends of the vibration transmitting element 104 to respectively abut against the vibration sensor 102 and the injection device 200.

The vibration transmitting element 104 may cover the surroundings of the vibration sensor.

The vibration sensor 102 may contact the inner surface of the bottom plate 103 and the injection device 200 may contact the outer surface of the bottom plate 103.

The processing unit 106 may include the circuit board 112 and the microprocessor (not illustrated) and may process the at least one vibration signal for generating the injected dose information corresponding to the injected dose.

The vibration signal may be generated by the relative movement between internal components of the injection device while the user sets the injected dose and the corresponding injected dose can be detected by the vibration signal.

Before storing the injected dose information, the injected dose detection device 10 may allow a user to confirm the detected injected dose information.

If the detected injected dose information is different from the injected dose that is set, the user may manually correct the incorrect injected dose information to achieve data accuracy.

The injected dose detection device 10 and the injected dose detection system 20 can reduce detection errors and improve detection accuracy.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An injected dose detection device, comprising:
a housing having a joint surface surrounding an injection device and a through hole formed on the joint surface configured to communicate with an internal part of the housing; a vibration sensor disposed in the internal part of the housing configured to detect at least one vibration signal based on a minimum vibration threshold;
a vibration transmitting element positioned directly between the vibration sensor and the injection device and configured to transmit the at least one vibration signal; and
a processing unit configured to process the at least one vibration signal for generating injected dose information corresponding to the injected dose, wherein
a bottom plate and a side wall of the vibration transmitting element form a shell structure to cover the vibration sensor.

2. The injected dose detection device of claim 1, further comprising:
a storage device electrically connected to the processing unit configured to store the injected dose information.

3. The injected dose detection device of claim 2, further comprising:
a wireless communication module electrically connected to the processing unit configured to wirelessly transmit the injected dose information to an electronic device.

4. The injected dose detection device of claim 3, further comprising:
a display electrically connected to the processing unit configured to display the injected dose information.

5. The injected dose detection device of claim 4, further comprising at least one adjusting button electrically connected to the processing unit configured to adjust the injected dose information.

6. The injected dose detection device of claim 5, further comprising:
a power switch electrically connected to the processing unit;
a battery electrically connected to the power switch, and
a light emitting diode electrically connected to the processing unit for indicating an operation status.

7. The injected dose detection device of claim 1, wherein the vibration sensor contacts the inner surface of the bottom plate, and the injection device contacts the outer surface of the bottom plate.

8. The injected dose detection device of claim 3, wherein the electronic device is a server, a smart phone, a laptop computer, or a personal computer.

9. The injected dose detection device of claim 5, wherein the processing unit is configured to change the minimum vibration threshold based on a frequency at which the at least one adjusting button is pressed, and the minimum vibration threshold is a minimum amplitude of the vibrational signal.

10. The injected dose detection device of claim 5, wherein
the at least one adjusting button comprises at least two adjusting buttons,
the minimum vibration threshold is decreased when one of the at least two adjusting buttons is pushed to increase the number of injected doses, and
the minimum vibration threshold is increased when a different one of the at least two adjusting buttons is pushed to decrease the number of injected doses.

11. An injected dose detection system, comprising:
an injection device; and
an injected dose detection device, comprising:
a housing having a joint surface surrounding the injection device and a through hole formed on the joint surface configured to communicate with an internal part of the housing;
a vibration sensor disposed in the internal part of the housing configured to detect at least one vibration signal based on a minimum vibration threshold;
a vibration transmitting element positioned directly between the vibration sensor and the injection device and configured to transmit the at least one vibration signal; and
a processing unit configured to process the at least one vibration signal for generating injected dose information corresponding to the injected dose, wherein
a bottom late and a side wall of the vibration transmitting element form a shell structure to cover the vibration sensor.

12. The injected dose detection system of claim 11, further comprising:
a storage device electrically connected to the processing unit configured to store the injected dose information.

13. The injected dose detection system of claim 12, further comprising:

a wireless communication module electrically connected to the processing unit configured to wirelessly transmit the injected dose information to an electronic device.

14. The injected dose detection system of claim 13, further comprising:
a display electrically connected to the processing unit configured to display the injected dose information.

15. The injected dose detection system of claim 14, further comprising at least one adjusting button electrically connected to the processing unit configured to adjust the injected dose information.

16. The injected dose detection system of claim 15, further comprising:
a power switch electrically connected to the processing unit;
a battery electrically connected to the power switch, and
a light emitting diode electrically connected to the processing unit for indicating an operation status.

17. The injected dose detection system of claim 11, wherein
the vibration sensor contacts the inner surface of the bottom plate, and the injection device contacts the outer surface of the bottom plate.

18. The injected dose detection system of claim 13, wherein the electronic device is a server, a smart phone, a laptop computer, or a personal computer.

19. The injected dose detection device of claim 15, wherein
the processing unit is configured to change the minimum vibration threshold based on a frequency at which the at least one adjusting button is pressed, and the minimum vibration threshold is a minimum amplitude of the vibrational signal.

20. The injected dose detection system of claim 15, wherein
the at least one adjusting button comprises at least two adjusting buttons,
the minimum vibration threshold is decreased when one of the at least two adjusting buttons is pushed to increase the number of injected doses, and
the minimum vibration threshold is increased when a different one of the at least two adjusting buttons is pushed to decrease the number of injected doses.

* * * * *